United States Patent [19]

Eichenauer et al.

[11] Patent Number: 4,922,031

[45] Date of Patent: May 1, 1990

[54] PREPARATION OF 4,4'-DIHYDROXYBIPHENYL

[75] Inventors: Ulrich Eichenauer, Frankfurt; Peter Neumann, Mannheim, both of Fed. Rep. of Germany

[73] Assignee: BASF Aktiengesellschaft, Ludwigshafen, Fed. Rep. of Germany

[21] Appl. No.: 299,476

[22] Filed: Jan. 23, 1989

[30] Foreign Application Priority Data

Jan. 23, 1988 [DE]  Fed. Rep. of Germany ....... 3801943

[51] Int. Cl.$^5$ ..................... C07C 39/14; C07C 37/04
[52] U.S. Cl. .................... 568/730; 568/738; 568/769; 568/795
[58] Field of Search ............... 568/769, 730, 729, 738, 568/795

[56] References Cited

U.S. PATENT DOCUMENTS

| | | | |
|---|---|---|---|
| 2,407,045 | 9/1945 | Tyrer | 568/769 |
| 2,773,908 | 12/1956 | Cake | 568/769 |
| 2,856,437 | 10/1958 | Cake | 568/769 |
| 4,243,822 | 6/1981 | Demler et al. | 568/769 |
| 4,465,878 | 8/1984 | Hashimoto | 568/795 |
| 4,467,123 | 8/1984 | Mayer et al. | 568/769 |
| 4,633,024 | 12/1986 | Ueno et al. | 568/769 |

FOREIGN PATENT DOCUMENTS

| | | |
|---|---|---|
| 0071420 | 9/1985 | European Pat. Off. |
| 810871 | 8/1951 | Fed. Rep. of Germany. |
| 1214118 | 12/1970 | United Kingdom ............... 568/769 |

OTHER PUBLICATIONS

Helvetica Chimica Acta vol. 14, 751–779 (1931).
J Chem. Soc. Perkin II, 1560 (1977).
Inoue et al., "Chemical Abstract", vol. 92; 41563d (1980).

*Primary Examiner*—Werren B. Lone
*Attorney, Agent, or Firm*—Oblon, Spivak, McClelland, Maier & Neustadt

[57] ABSTRACT

4,4'-dihydroxybiphenyl is prepared by treating biphenyl-4,4'-disulfonic acid or one of its alkali metal salts in an alkali metal hydroxide melt by a process in which the treatment is carried out in a melt which contains from 7 to 14 moles of potassium hydroxide and from 0 to 8 moles of sodium hydroxide, based in each case on 1 mole of biphenyl-4,4'-disulfonic acid, in the presence of an alkali metal carbonate at from 280° to 360° C.

5 Claims, No Drawings

PREPARATION OF 4,4'-DIHYDROXYBIPHENYL

The present invention relates to a novel process for the preparation of 4,4'-dihydroxybiphenyl by treating biphenyl-4,4'-disulfonic acid or one of its alkali metal salts in an alkali metal hydroxide melt at from 200° to 340° C., the melt containing potassium hydroxide, if required sodium hydroxide, and an alkali metal carbonate.

The preparation of 4,4'-dihydroxybiphenyl by treating the corresponding disulfonic acid in an alkali metal hydroxide melt is known. It is generally carried out under superatmospheric pressure in the presence of water (DE-A- No. 3 204 079, EP-A-No.85 883) or of a high boiling chlorohydrocarbon (EP-A-No.92 772). However, expensive apparatus is required.

Reactions in the melt which are carried out under atmospheric pressure are also known. For example, J. Chem. Soc. Japan, 84 (1963), 143 describes the reaction of 1 mole of a dipotassium salt of biphenyl-4,4'-disulfonic acid with 12.5 moles of potassium hydroxide and 8.9 moles of sodium hydroxide at 330° C. The end product is obtained in a yield of 19% after purification.

U.S. Pat. No. 4,243,822 describes the use of 12.5 moles of potassium hydroxide per mole of the dipotassium salt of biphenyl-4,4'-disulfonic acid at from 335° to 340° C. The disadvantage here is the large excess of expensive potassium hydroxide.

According to JP-A-No. 112 844/1979, the reaction should be carried out in pure sodium hydroxide. This reaction requires a temperature of 380° C., which, however, cannot be reached using conventional heat transfer media.

A general disadvantage of these alkali metal hydroxide melts is their foaming, which, at the high viscosity of the melt, is caused by the water formed during the reaction. To reduce the viscosity of alkali metal melts, additives such as sodium acetate (JP-A- No. 8720/1960) or carbon, alkali metal sulfites, alkali metal sulfates or alkaline earth metal hydroxides (DE-B No. 815 645) have been proposed.

DE-A-No.3 266 391 discloses the reaction of 1 mole of the dipotassium salt of biphenyl-4,4'-disulfonic acid with 8 moles of potassium hydroxide in the presence of 0.75 mole of potassium sulfate. The reaction is carried out in a ball mill.

In the prior art processes, however, the problem of foaming is not solved.

It is an object of the present invention to provide a process for the preparation of 4,4'-dihydroxybiphenyl by treating biphenyl-4,4'-disulfonic acid or one of its alkali metal salts in an alkali metal hydroxide melt, which can be carried out without very expensive apparatus and in which foaming of the alkali metal hydroxide melts is suppressed We have found that this object is achieved and that 4,4'-hydroxybiphenyl can be advantageously prepared by treating biphenyl-4,4'-disulfonic acid or one of its alkali metal salts in an alkali metal hydroxide melt if the treatment is carried out in a melt which contains from 7 to 14 moles of potassium hydroxide and from 0 to 8 moles of sodium hydroxide, based in each case on 1 mole of biphenyl-4,4'-disulfonic acid, in the presence of an alkali metal carbonate at from 280° to 360° C.

In the novel process, in addition to the biphenyl-4,4'-disulfonic acid it is also possible to react its dialkali metal salts, for example the dilithium, disodium or dipotassium salts.

The preparation of the starting materials is known and is carried out, for example, by sulfonation of biphenyl with oleum, sulfuric acid or chlorosulfonic acid (cf. for example J. Chem. Soc., Perkin II, (1977), 1560). The alkali metal sulfonates can be prepared from the sulfonating mixtures by salting out (Helv. Chem. Acta 14 (1931), 751) or neutralization.

The novel process is advantageously carried out in such a way that a melt which contains from 7 to 14 moles of potassium hydroxide and from 0 to 8, preferably from 0 to 4, moles of sodium hydroxide, based in each case on 1 mole of biphenyl-4,4'-disulfonic acid, and an alkali metal carbonate is prepared.

Examples of suitable alkali metal carbonates are lithium carbonate, sodium carbonate or potassium carbonate. Preferably from 10 to 100, in particular from 50 to 100, mol % of alkali metal carbonate are used per mole of biphenyl-4,4'-disulfonic acid. The use of sodium carbonate is particularly preferred.

The melt is heated to 280°–360° C., preferably 300°–340° C., in particular about 320° C.

The temperature according to the invention is maintained and the biphenyl-4,4'-disulfonic acid or one of its dialkali metal salts is metered into the melt. The substance may be metered as such, in aqueous solution or in solution in sulfuric acid.

Preferably, a 20–50% strength by weight aqueous solution of biphenyl-4,4'-disulfonic acid which is at 20°14 100° C., preferably 40°–100° C., is metered into the melt.

The addition of a solution of biphenyl-4,4'-disulfonic acid in 30–70% strength by weight sulfuric acid to the melt is also preferred. The concentration of biphenyl-4,4'-disulfonic acid in the solution is from 20 to 50% by weight, based on the weight of the solution, and this temperature is from 20° to 100° C., preferably from 40° to 100° C.

The addition of a dialkali metal salt of biphenyl-4,4'-disulfonic acid as such is also preferred. With the exception of the last-mentioned case, the water introduced into the melt and/or formed during the neutralization reaction is distilled off.

During the reaction, which generally takes from 2 to 6 hours, the melt should as a rule have a water content of from 10 to 20, preferably about 15, % by weight, based on the total weight of the melt. The water content can be adjusted by recycling some of the water distilled off.

After the reaction has ended, the reaction mixture is cooled by metering in water and simultaneously reducing the temperature of the melt (for example by reducing the heating bath temperature). It should be ensured that the boiling point of the mixture is not exceeded. Concentrated hydrochloric acid is added at about 90° C. to the reaction mixture diluted in this way with water, until a pH of 6.5-6.7 is obtained, and the 4,4'-dihydroxbiphenyl thus liberated is obtained by means of filtration.

The crude 4,4'-dihydroxybiphenyl obtained as the filtration residue can be purified by extraction. Examples of suitable extracting agents are alcohols, such as methanol, ethanol or isopropanol, ketones, such as acetone or methyl ethyl ketone, and esters, such as ethyl acetate.

The novel process gives 4,4'-dihydroxybiphenyl in good yield and high purity. Because of the presence of an alkali metal carbonate, the foam formation mentioned, which represents a safety risk in a process carried out on the industrial scale, is surprisingly suppressed.

4,4'-Dihydroxybiphenyl is a useful intermediate. It is used, for example, as a monomer component for polyesters or is required for the preparation of photographic developers.

The Examples which follow illustrate the invention.

EXAMPLE 1

400 g (6.1 moles) of potassium hydroxide having a water content of 15% by weight and 40 g (0.38 mole) of sodium carbonate were initially taken in a stirred 1 l V2A stainless steel kettle and 195 g (0.5 mole) of the dipotassium salt of biphenyl-4,4'-disulfonic acid were introduced at 280° C. The temperature was then increased to 320° C., this temperature was maintained for 3 hours and the melt was cooled by constantly metering in water and simultaneously reducing the heating bath temperature. The reaction mixture was diluted with water and acidified with concentrated hydrochloric acid at 90° C. to a pH of 6.5. The resulting precipitate was filtered off under suction, and 4,4'-dihydroxybiphenyl was extracted by means of acetone. The extracting agent was removed to give 85.5 g (92%) of 4,4'-dihydroxybiphenyl, which had a purity of >99% (HPLC).

The Examples below were carried out similarly. Instead of potassium hydroxide, however, a mixture of potassium hydroxide and sodium hydroxide was used in each case.

| Example No. | Alkali metal hydroxide [mole] | | Yield [%] | Purity [%] |
| --- | --- | --- | --- | --- |
| | KOH | NaOH | | |
| 2 | 5.2 | 1.5 | 86 | 99.6 |
| 3 | 4.6 | 2.5 | 80 | 99.7 |
| 4 | 4.3 | 3 | 58 | 99.6 |

We claim:
1. A process for the preparation of 4,4'-dihydroxybiphenyl by treating biphenyl-4,4'-disulfonic acid or one of its alkali metal salts in an alkali metal hydroxide melt, wherein the treatment is carried out in a melt which contains from 7 to 14 moles of potassium hydroxide and from 0 to 8 moles of sodium hydroxide, based in each case on 1 mole of biphenyl-4,4'-disulfonic acid, in the presence of an alkali metal carbonate at from 280 to 360° C.

2. A process as claimed in claim 1, wherein the treatment is carried out at from 300° to 340° C.

3. A process as claimed in claim 1, wherein the treatment is carried out in the presence of from 10 to 100 mol % of an alkali metal carbonate per mole of biphenyl-4,4'-disulfonic acid.

4. A process as claimed in claim 1, wherein the treatment is carried out in the presence of sodium carbonate.

5. A process as claimed in claim 1, wherein the treatment is carried out in a melt which contains from 7 to 14 moles of potassium hydroxide and from 0 to 4 moles of sodium hydroxide, based in each case on 1 mole of biphenyl-4,4'-disulfonic acid.

* * * * *